United States Patent [19]

Koch et al.

[11] 4,175,947
[45] Nov. 27, 1979

[54] PHENOXY-PHENOXYPROPIONIC ACID ESTERS

[75] Inventors: Manfred Koch, Kelkheim; Reinhard Handte, Hofheim; Gerhard Hörlein, Frankfurt am Main; Hermann Bieringer, Eppstein; Peter Langelüddeke, Hofheim, all of Fed. Rep. of Germany

[73] Assignee: Hoechst Aktiengesellschaft, Frankfurt am Main, Fed. Rep. of Germany

[21] Appl. No.: 789,673

[22] Filed: Apr. 21, 1977

[30] Foreign Application Priority Data

Apr. 23, 1976 [DE] Fed. Rep. of Germany ....... 2617804

[51] Int. Cl.$^2$ .......................... A01N 9/24; A01N 9/28; C07C 69/76; C07D 307/24
[52] U.S. Cl. .............................................. 71/88; 71/92; 71/94; 71/95; 71/98; 71/103; 71/108; 71/109; 260/326.43; 260/340.9 R; 260/347.4; 260/348.49; 544/171; 544/399; 546/239; 546/342; 560/20; 560/33; 560/62; 560/63
[58] Field of Search .................. 260/347.4, 340.9 R, 260/348.49; 560/62, 63, 33; 71/88, 108, 109, 98, 103

[56] References Cited

U.S. PATENT DOCUMENTS

| | | | |
|---|---|---|---|
| 2,728,653 | 12/1955 | Scott | 260/347.4 X |
| 3,721,703 | 3/1973 | Nahm et al. | 560/62 X |
| 3,954,442 | 5/1976 | Becker et al. | 560/62 X |
| 3,968,143 | 7/1976 | Schacht et al. | 560/62 X |
| 4,070,177 | 1/1978 | Nishiyama et al. | 560/62 X |
| 4,070,178 | 1/1978 | Johnson et al. | 560/62 X |

FOREIGN PATENT DOCUMENTS

2531643 1/1976 Fed. Rep. of Germany.

OTHER PUBLICATIONS

Troesken et al., Chemical Abstracts, vol. 84 (1976), 116,948d.
Takahashi et al., Chemical Abstracts, vol. 84 (1976) 164,453k.

*Primary Examiner*—Richard Raymond
*Attorney, Agent, or Firm*—Curtis, Morris & Safford

[57] ABSTRACT

Phenoxy-phenoxypropionic acid derivatives of the formula

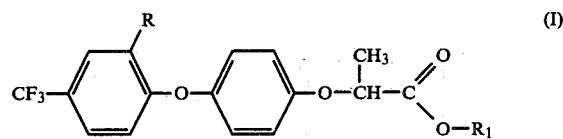

(I)

wherein R is hydrogen or halogen, and $R_1$ is substituted alkyl, cyclohexenyl, phenylalkenyl or (substituted) alkinyl, are interesting selective herbicides having a special activity against weed grasses. They are obtained for example by reaction of corresponding phenoxypropionic acid halides with hydroxy compounds of the formula HO—$R_1$.

20 Claims, No Drawings

PHENOXY-PHENOXYPROPIONIC ACID ESTERS

The present invention provides novel 2-[4'-phenoxy]-propionic acid derivatives of the formula

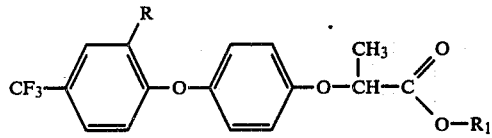

wherein
R is hydrogen or halogen,
$R_1$ is
(a) linear or branched $(C_1-C_{12})$-alkyl substituted by cyclohexyl, halogenophenyl, nitrophenyl, $(C_1-C_6)$-alkylphenyl, phenoxy optionally mono- to tri-substituted by halogen and/or $(C_1-C_4)$-alkyl; $(C_5-C_6)$-alkoxy, $(C_5-C_6)$-alkoxy-$(C_2-C_4)$-alkoxy, $(C_1-C_4)$-alkoxyethoxyethoxy, $(C_1-C_4)$-acyl, a radical of the formulae

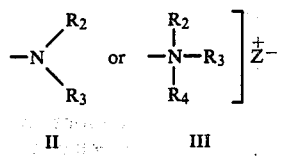

or mono- or polysubstituted by phenyl in 2-position or a more remote position to the carboxyl group;
(b) cyclohexenyl or phenyl-$(C_3-C_4)$-alkenyl;
(c) $(C_3-C_4)$-alkinyl, optionally mono- or disubstituted by linear or branched $(C_1-C_4)$-alkyl, halogen, phenyl, halogenophenyl or $(C_1-C_4)$-alkylphenyl with the proviso that $R_1$ cannot be an unsubstituted propargyl or butinyl radical;
(d) a radical of the formulae

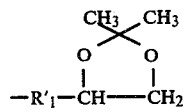 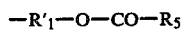

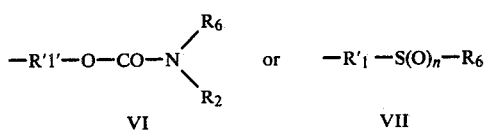 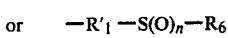 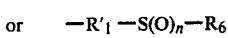

or
(e) $(C_1-C_2)$-alkyl substituted by furyl, tetrahydrofuryl, pyridyl or oxiranyl;
$R_2$ is hydrogen, $(C_1-C_4)$-alkyl or $(C_1-C_4)$-alkoxy,
$R_3$ is hydrogen, $(C_1-C_4)$-alkyl or phenyl,
$R_2$ and $R_3$ together are a saturated or unsaturated alkylene chain having 4 or 5 members, wherein a methylene group may be replaced by —O—,

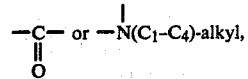

$R_4$ is hydrogen or $(C_1-C_4)$-alkyl,
Z is the anion of an organic or inorganic acid,
$R_1'$, is linear or branched $(C_1-C_{12})$-alkylene,
$R_5$ is hydrogen, $(C_1-C_4)$alkyl, $(C_1-C_4)$-halogenoalkyl, phenyl optionally substituted by halogen, nitro and/or $(C_1-C_4)$-alkyl, or a radical of the formulae

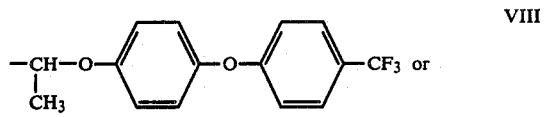

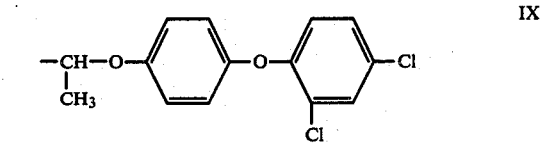

$R_6$ is $(C_1-C_4)$-alkyl and
n is 0, 1 or 2.
Examples of radicals of the formula

wherein
$R_2$ and $R_3$ are a closed chain are the following:

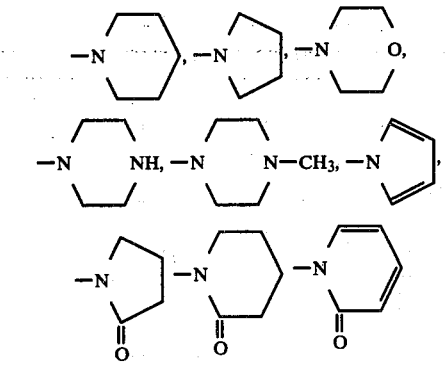

Corresponding groups may occur also in the radicals of the formulae II and III.
By "halogen", there is to be understood preferably fluorine, chlorine and/or bromine, $Z^-$ represents especially $Cl^-$, $Br^-$, $HSO_4^-$, methane sulfonate, ethane sulfonate, p-toluenesulfonate, acetate or trichloroacetate.
Especially preferred are those compounds of the formula I, wherein $R_1$ is
(a) a linear or branched $(C_1-C_6)$-alkyl mono- to tri-substituted by a radical of the formulae II or III, $(C_1-C_4)$acyl or, in 2-position or a more remote position to the carboxyl group, by phenyl or phenoxy optionally substituted by methyl and/or chlorine
(b) cyclohexyl or phenyl(C$_3$–C$_4$)alkenyl;
(c) (C$_3$–C$_4$)alkinyl mono- or disubstituted in 1-position by (C$_1$–C$_4$)alkyl and/or phenyl;
(d) a radical or the formulae IV or V, wherein R$_1'$, represents linear or branched (C$_1$–C$_6$)alkylene;
(e) a radical of the formulae

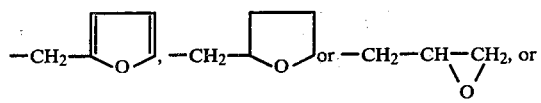

R$_2$ is hydrogen or (C$_1$–C$_4$)alkyl,
R$_2$ and R$_3$ together are an alkylene chain having 4 or 5 carbon atoms, wherein a methylene group may be replaced by —O— or —CO—;
R$_5$ is (C$_1$–C$_4$)alkyl, (C$_1$–C$_4$)halogenoalkyl or a radical of the formula VIII or IX, and
n is zero, and wherein
R, R$_3$, R$_4$, R$_6$ and Z$^-$ are as defined above.

The compounds of the invention are prepared according to methods known for analogous compounds. They are obtained for example
 (a) by reaction of 2-(4'-phenoxyphenoxy)-propionic acid halides of formula X which are easily obtained by halogenation of the corresponding acid with compounds of formula XI in the presence or absence of acid-binding agents according to the following scheme:

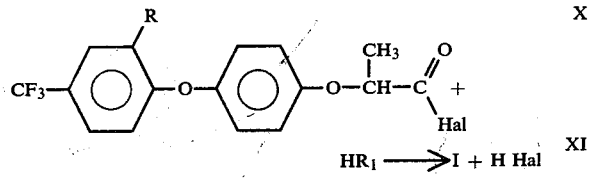

(When compounds of formula XI are used in which the radical R$_1$ is substituted by a radical of the formula II or III, they may be reacted without the addition of acid-binding agents. The compounds of the formula XI are used for the reaction in the form of their hydrohalides especially in the case where one of the radicals R$_2$ or R$_3$ or both these radicals are hydrogen.)
 (b) by reaction of corresponding 2-(4'-phenoxyphenoxy)-propionic acids with alcohols of formula XI under acidic catalysis;
 (c) by reaction of corresponding 4-phenoxyphenols with 2-halogeno-propionic acid esters of formula XII under basic conditions according to the following scheme:

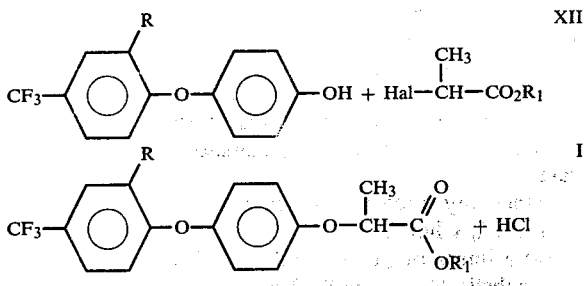

(d) by reaction of salts of corresponding 2-(4'-phenoxyphenoxy)-propionic acids (formula I, R$_1$=H) with halogen-substituted compounds of the formula Hal-R$_1$.

By subsequent alteration of the esters of the formula I by means of alkylation, acylation or oxidation, further compounds of formula I may be obtained. For example, esters substituted in the ester radical by hydroxy, mercapto or amino groups may be alkylated or acylated according to known methods, or thioether groups present in the ester radical may be oxidized in known manner to form sulfine or sulfone groups.

The compounds of the present invention have a wide spectrum of herbicidal action against annual and perennial weed grasses; simultaneously, they are well tolerated by dicotyledonous crop plants, and can therefore be used for selectively combating weed grasses in crop plants. They are especially suitable because of their high efficiency for combating creeping wheat, Bermuda grass and other perennial weed grasses in orchards, vineyards etc.

The present invention provides furthermore herbicidal compositions which comprise a content of compounds of the formula I in addition to usual formulation auxiliaries and inert materials, and the use of compounds of the formula I for combating weed grasses.

The compositions of the present invention generally contain from 2 to 95% by weight of the active substance of the formula I. They may be used in the form of wettable powders, emulsifiable concentrates, sprayable solutions, dusting preparations or granulates in usual formulations.

Wettable powders are preparations capable of being dispersed uniformly in water, which contain, in addition to the active substance and a diluent or inert substance, wetting agents, for example, polyoxethylated alkylphenols, polyoxethylated oleyl- or stearyl-amines, alkylsulfonates or alkylphenylsulfonates and dispersing agents, for example, sodium lignin sulfonate, sodium 2,2'-dinaphthylmethane-6,6'-disulfonate, or sodium oleylmethyl-taurinate.

Emulsifiable concentrates are obtained by dissolving the active substance in an organic solvent, for example, butanol, cyclohexanone, dimethylformamide, xylene or a high boiling aromatic compound.

Dusting preparations are obtained by grinding the active substance with finely divided solid substances, for example, talcum, natural clays, such as kaolin, bentonite, pyrophyllite or diatomaceous earth.

Sprayable solutions, which are often marketed in spraying cans, contain the active substance dissolved in an organic solvent, as well as, for example, a mixture of fluorochlorohydrocarbons as propellant.

Granulates can be prepared either by spraying the active substance onto an absorptive granulated inert material or by applying concentrates of the active substance by means of adhesives, for example, polyvinyl alcohol, sodium polyacrylate or mineral oils, onto the surface of carrier substances, such as sand, kaolinites, or of granulated inert material. Also, suitable active substances may be formulated in the manner usual for producing fertilizer granules, if desired in admixture with fertilizers.

In the herbicidal compositions, the concentrations of the active substances in the ordinary commercial formulations may vary. In wettable powders the concentration of active substance varies, for example, between about 10% and 80%, the remainder consisting of the formulation additives mentioned above. In the case of emulsifiable concentrates the concentration of active substance is about 10% to 60%. Dusting formulations contain generally from 5 to 20% of active substance, and sprayable solutions contain about 2 to 20%. In the case of granulates, the content of active substance depends in part on whether the active compound is present in liquid or solid form and on what granulating auxiliaries, fillers, etc. are used.

For use, the ordinary commercial concentrates may be diluted in usual manner, for example, with water in the case of wettable powders and emulsifiable concentrates. Dusting and granulated preparations and sprayable solutions are not diluted with further inert substances before use. The quantities required for use vary with the external conditions such as temperature and humidity. They may vary within wide limits, for example, between 0.1 and 10.0 kg of active substance per hectare, but preferably between 0.3 and 3 kg per hectare.

The active substances of the invention may be combined with other herbicides and soil insecticides. Herbicides suitable for blending are the following compounds:

| | |
|---|---|
| Urea derivatives: | linuron, chloroxuron, monolinuron, fluometuron, diuron; |
| Triazine derivatives: | simazine, atrazine, ametryne, prometryne, desmetryne, methoprotryne; |
| Uracil derivatives: | lenacil, bromacil; |
| Pyrazone derivatives: | 1-phenyl-4-amino-5-chloropyridazone-(6); |
| Growth preparations: | 2,4-dichloro-phenoxy-acetic acid, 4-chloro-2-methylphenoxy-acetic acid, 2,4,5-trichlorophenoxy-acetic acid, 4-chloro-2-methyl-phenoxy-butyric acid, 2,3,6-trichlorobenzoic acid; |
| Carbamic acid derivatives: | barban, phenmedipham, diallate, triallate, vernolate and 2-chloro-allyl-N,N-diethyl-dithiocarbamate, Swep; |
| Dinitrophenol derivatives: | dinitro-o-cresol, dinoseb, dinoseb acetate; |
| Chlorinated aliphatic acids: | sodium chloracetate, dalapon; |
| Amides: | diphenamide, N,N-diallyl-chloroacetamide; |
| Dipyridilium compounds: | paraquat, diquat, morfamquat; |
| Anilides: | N-(3,4-dichlorophenyl)-methacrylamide, propanil, solane, monalide, 2-chloro-2',6'-diethyl-N-(methoxymethyl)-acetanilide, propachlor; |
| Nitriles: | dichlobenil, ioxynil; |
| other preparations: | flurenol, 3,4-dichloropropion-anilide, trifluraline, bensulide, monosodium methylarsonate, 4-trifluoromethyl-2,4'-dinitro-diphenyl ether. |

EXAMPLES OF FORMULATION

EXAMPLE A

An emulsifiable concentrate is obtained from:
15 parts by weight of active substance
75 parts by weight of cyclohexanone as solvent
10 parts by weight of oxyethylated nonylphenol (10 EO) as emulsifier.

EXAMPLE B

A dusting powder is obtained by mixing
10 parts by weight of active substance
90 parts by weight of talcum as inert substance and pulverizing the whole in a cross-beater mill.

EXAMPLE C

A wettable powder readily dispersable in water is obtained by mixing
25 parts by weight of active substance
64 parts by weight of kaolin-containing quartz as inert substance
10 parts by weight of potassium lignin sulfonate and
1 part by weight of sodium oleylmethyl tauride as wetting and dispersing agent
and grinding the whole in a disk attrition mill.

EXAMPLE D

A granulate consists, e.g. of approximately
2-15 parts by weight of active substance
98-85 parts by weight of inert granulate carrier material such as, for example, atapulgit, pumice and quartz sand.

EXAMPLE 1

2-[4'-(4''-trifluoromethylphenoxy)-phenoxy]-propionic acid-(2-methylmercaptoeth-1-yl)ester 32.5 g=0.1 mol of 2-[4'-(4''-trifluoromethylphenoxy)-phenoxy]-propionic acid, 9.2 g=0.1 mol of 2-methylmercaptoethanol and 2 ml of concentrated sulfuric acid are refluxed in 60 ml of chloroform with azetropic distilling-off of the water of reaction. After cooling, the batch is washed with water, subsequently with bicarbonate solution and finally once again with water. After drying over calcium chloride, the solvent is removed and the residue is distilled under highly reduced pressure.

33.2 g=83% of the theoretical yield of 2-[4'-(4''-trifluoromethylphenoxy)-phenoxy]-propionic acid-(2-methylmercaptoeth-1-yl)ester having a refractive index of $n_D=1.5248$ are obtained.

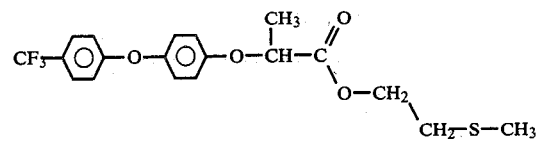

EXAMPLE 2

2-[4'-(4''-trifluoromethylphenoxy)-phenoxy]-propionic acid-(3-methylpent-1-in-3-yl)ester 0.1 mol=34.8 g of 2-[4'-(4''-trifluoromethylphenoxy)-phenoxy]-propionic acid chloride is added dropwise to a solution of 9.3 g=0.095 mol of 3-hydroxy-3-methyl-pent-1-ine and 0.1 mol=10.1 g of triethylamine in 80 ml of toluene. The salt precipitate is filtered off, and the toluenic solution is washed with sodium bicarbonate solution and water. After drying over sodium sulfate, the solvent is distilled off under reduced pressure.

33.4 g=89% of the theoretical yield of 2-[4'-(4''-trifluoromethylphenoxy)-phenoxy]-propionic acid-(3-methylpent-1-in-3-yl)ester are obtained having a refractive index $n_D^{23}=1.5069$.

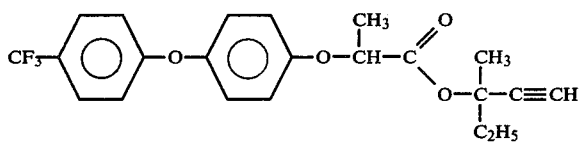

EXAMPLE 3

2-[4'-(4''-trifluoromethylphenoxy)-phenoxy]-propionic acid-(2-dimethylamino-eth-1-yl)ester 0.08 mol = 27.56 g of 2-[4'-(4''-trifluoromethylphenoxy)-phenoxy]-propionic acid chloride dissolved in 30 ml of toluene are added dropwise at room temperature to a solution of 0.08 mol = 7.12 g of 2-dimethylamino-ethanol in 50 ml of absolute toluene. Subsequently, the batch is agitated for 1 hour at 50° C. 100 ml of 1 n sodium carbonate solution are then added, and agitation is continued for 1 hour at room temperature. After washing with water and drying over Na$_2$SO$_4$, toluene is distilled off, and the oily residue is distilled under highly reduced pressure.

27.95 g = 88% of the theoretical yield of 2-[4'-(4''-trifluoromethylphenoxy)-phenoxy]-propionic acid-(2-dimethylaminoeth-1-yl)ester having a boiling point of 165° C. at 0.08 mm Hg are obtained.

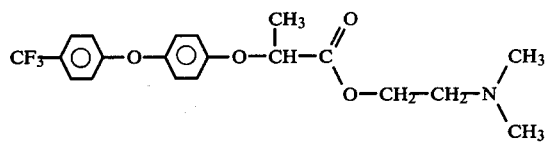

EXAMPLE 4

2-[4'-(4''-trifluoromethylphenoxy)-phenoxy]-propionic acid-(2-methylsulfonyleth-1-yl)ester A solution of 32 g of 3-chloroperbenzoic acid (65% strength) in chloroform is added dropwise without cooling to a solution of 20 g = 0.05 mol of 2-[4'-(4''-trifluoromethylphenoxy)-phenoxy]-propionic acid-(2-methylmercaptoeth-1-yl)ester (Example 3) in 40 ml of chloroform, which corresponds to 0.12 mol of active substance. Subsequently, the batch is refluxed for ½ hour. After cooling of the solution, the precipitate is filtered off and the chloroform solution is washed with sodium bicarbonate solution and water. After drying over sodium sulfate and removal of the solvent, 19.9 g = 92% of the theoretical yield of 2-[4'-(4''-trifluoromethylphenoxy)-phenoxy]-propinonic acid-(2-methylsulfonyleth-1-yl)ester having a refractive index $n_D^{23} = 1.5215$ are obtained.

$$CF_3-\underset{}{\bigcirc}-O-\underset{}{\bigcirc}-O-\overset{CH_3}{\underset{}{CH}}-\overset{O}{\underset{}{C}}\diagdown O-CH_2-CH_2-\overset{O}{\underset{O}{S}}-CH_3$$

EXAMPLE 5

2-[4'-(4''-trifluoromethylphenoxy)-phenyl]-propionic acid-(2-chloroacetoxyeth-1-yl)-ester 0.05 mol = 18.5 g of 2-[4'-(4''-trifluoromethylphenoxy)-phenoxy]-propionic acid-glycol semi-ester (Example 2) and 0.055 mol = 5.5 g of triethylamine are dissolved in 80 ml of toluene. 6.2 g = 0.055 mol of chloroacetyl chloride are added dropwise, and subsequently, the batch is stirred for 1 hour at 50° C. After having filtered off the salt precipitate, the solution is washed with bicarbonate solution and water, and dried over sodium sulfate. After removal of the toluene and subsequent distillation under highly reduced pressure, 17.8 g = 80% of the theoretical yield of 2-[4'-(4''-trifluoromethylphenoxy)-phenoxy]-propionic acid-(2-chloroacetoxyeth-1-yl)ester having a boiling point of 165° C. at 0.08 mm Hg are obtained.

$$CF_3-\underset{}{\bigcirc}-O-\underset{}{\bigcirc}-O-\overset{CH_3}{\underset{}{CH}}-\overset{O}{\underset{}{C}}\diagdown O-CH_2-CH_2-O-\overset{O}{\underset{}{C}}-CH_2-Cl$$

For an acylation with isocyanates, a prolonged heating, generally for about 8 hours, is required.

In analogous manner, there are prepared (see Table):

TABLE

| Example No. | R | R$_1$ | m.p./b.p/n$_D$ | acc. to Example |
|---|---|---|---|---|
| 6 | H | —CH$_2$—CH$_2$—O—C(=O)—CH(CH$_3$)—O—⌬—O—⌬—CF$_3$ | $n_D^{21.5}$:1.5211 | 5 |
| 7 | H | —CH$_2$—CH$_2$—SCH(CH$_3$)$_2$ | $n_D^{22}$:1.5175 | 2 |
| 8 | H | —CH$_2$—CH$_2$—(pyridyl) | $n_D^{24}$:1.5294 | 2 |

TABLE-continued

Structure: CF$_3$-substituted phenyl ring (with R ortho) — O — phenyl — O — CH(CH$_3$) — C(=O) — O — R$_1$

| Example No. | R | R$_1$ | m.p./b.p/n$_D$ | acc. to Example |
|---|---|---|---|---|
| 9 | H | —CH$_2$—CH$_2$—N(morpholine) | n$_D^{26}$:1.5153 | 3 |
| 10 | | —CH(CH$_3$)—CO—CH$_3$ | n$_D^{24}$:1.5070 | 2 |
| 11 | H | —CH$_2$—CH$_2$—O—C(=O)—NH—phenyl | m.p. 76°–77° C. | 5 |
| 12 | H | —CH$_2$—CH(epoxide)—CH$_2$ | n$_D^{25}$:1.5168 | 2 |
| 13 | H | —CH$_2$—(furan) | — | 2 |
| 14 | H | —CH$_2$—(tetrahydrofuran, H on carbon) | m.p. 57°–58° C. | 2 |
| 15 | H | —CH$_2$—CH$_2$—N(C$_2$H$_5$)$_2$ | n$_D^{24}$:1.5010 | 3 |
| 16 | H | —CH$_2$—CH$_2$—N$^+$(CH$_3$)$_3$J$^-$ | m.p. 74°–76° C. | 3 |
| 17 | H | —CH$_2$—CH$_2$—O—phenyl | n$_D^{23}$:1.5356 | 2 |
| 18 | H | —CH$_2$—CH=CH—phenyl | b.p.o,1:214° C. | 2 |
| 19 | H | —CH$_2$—CH$_2$—CH$_2$—phenyl | n$_D^{25}$:1.5306 | 2 |
| 20 | H | —CH(phenyl)—C≡CH | n$_D^{23}$:1.5402 | 2 |
| 21 | H | phenyl | n$_D^{24}$:1.5159 | 2 |
| 22 | H | —C(CH$_3$)$_2$—C≡CH | | 2 |
| 23 | H | —C(C$_2$H$_5$)$_2$—C≡CH | | 2 |
| 24 | H | —C(C$_3$H$_7$(n))(CH$_3$)—C≡CH | | 2 |
| 25 | H | —CH(4-chlorophenyl)—C≡CH | | 2 |

TABLE-continued

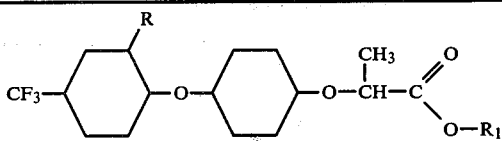

| Example No. | R | R₁ | m.p./b.p/n$_D$ | acc. to Example |
|---|---|---|---|---|
| 26 | H | $-\underset{\underset{C_6H_5}{\vert}}{\overset{\overset{CH_3}{\vert}}{C}}-C\equiv CH$ | | 2 |
| 27 | H | $-CH_2-CH_2-O-$(2-Cl, 4-Cl phenyl) | | 2 |
| 28 | H | $-CH_2-CH_2-O-$(2-CH₃, 4-Cl phenyl) | | 2 |
| 29 | H | $-CH_2-\underset{\underset{}{}}{\overset{\overset{CH_3}{\vert}}{CH}}-O-$(2-Cl, 4-Cl phenyl) | $n_D^{26}$:1.5473 | 2 |
| 30 | H | $-CH_2-\underset{\underset{}{}}{\overset{\overset{CH_3}{\vert}}{CH}}-O-$(2-CH₃, 4-Cl phenyl) | $n_D^{26}$:1.5330 | 2 |
| 31 | H | $-CH(C_2H_5)C\equiv CH$ | $n_D^{26}$:1.5054 | 2 |
| 32 | H | $-CH(n-C_3H_7)C\equiv CH$ | | 2 |
| 33 | H | $-CH_2-CH_2-N$(2-oxopiperidinyl) | $n_D^{22}$:1.5258 | 2 |
| 34 | H | $-CH_2-CH-CH_2$ with $O\underset{\underset{CH_3}{}}{\overset{\overset{}{}}{C(CH_3)_2}}O$ (dioxolane) | $n_D^{22}$:1.5025 | 2 |
| 35 | H | $CH_2-CH_2-O-CH_2-CH_2-O-CH_2(CH_2)_4-CH_3$ | $n_D^{24}$:1.4923 | 4 |
| 36 | H | $-CH_2-CH_2-(O-CH_2-CH_2)_2-OCH_3$ | b.p.$_{0.025}$:193° | 4 |
| 37 | H | $-CH_2-CH_2-(O-CH_2-CH_2)_2-OC_2H_5$ | | 4 |
| 38 | H | $-\underset{\underset{CH_3}{\vert}}{\overset{\overset{CH_3}{\vert}}{C}}-\overset{\overset{O}{\Vert}}{C}-CH_3$ | $n_D^{24}$:1.5128 | 2 |

BIOLOGICAL EXAMPLES

EXAMPLE I

Seeds of various grasses were sown in pots and the preparations according to the invention formulated as wettable powders were sprayed in different quantities onto the surface of the soil. The pots where then placed in a greenhouse for 4 weeks. The result of treatment (also in the case of the following examples) was determined by assessment according to Bolle's scheme (Nachrichtenblatt des Deutschen Pflanzenshcutzdienstes 16, 1964, 92–94):

| | Harmfull effect in % on | |
|---|---|---|
| Number | Weeds | Crop plants |
| 1 | 100 | 0 |
| 2 | 97.5 to 100 | >0 to 2.5 |
| 3 | 95 to <97.5 | >2.5 to 5 |
| 4 | 90 to <95 | 5 to 10 |
| 5 | 85 to 90 | 10 to 15 |
| 6 | 75 to 85 | 15 to 25 |
| 7 | 65 to 75 | 25 to 35 |
| 8 | 32.5 to 65 | 35 to 67.5 |
| 9 | 0 to 32.5 | 67.5 to 100 |

The procedure was the same with the herbicidal comparison agents used, Flurodifen (4-nitrophenyl-(2'-nitro-4'-trifluoromethylphenyl)-ether) and Mecoprop (2-(4'-chloro-2'-methylphenoxy)-propionic acid. The results collated in Table I show that the claimed compounds are considerably more effective against grasses than the two herbicides used for comparison. Further, the compounds from the other Examples had a similar effect against grasses.

TABLE I

| Compound of Example | (Pre-emergence treatment) | | | | |
|---|---|---|---|---|---|
| | kg/ha A.S. | CDN | SAL | LOM | AGR |
| 1 | 5 | 1 | 1 | 1 | 1 |
| | 1.2 | — | 1 | 1 | 1 |
| 3 | 5 | 1 | 1 | 1 | 1 |
| | 1.2 | — | 1 | 1 | — |
| 12 | 5 | 1 | 1 | 1 | 1 |
| | 1.2 | — | 1 | 1 | — |
| 20 | 5 | 1 | 1 | 1 | 2 |
| | 1.2 | — | 1 | 1 | — |
| 21 | 5 | 2 | 2 | 3 | 2 |
| | 1.2 | — | 2 | 4 | — |
| Fluorodifen | 2.5 | — | 3 | 5 | — |
| | 0.6 | 9 | 5 | 8 | 9 |
| Mecoprop | 2.5 | — | 3 | 5 | — |
| | — | — | 6 | 8 | — |

AVF = Avena fatua
SAL = Setaria lutescens
LOM = Lolium perenne
AGR = Agropyron repens
CDN = Cynodon dactylon

EXAMPLE II

Seeds of annual grasses were sown in pots and placed in a greenhouse for growing. 3 Weeks after sowing, the preparations according to the invention formulated as wetting powders were sprayed in various dosages on the plants, and their effect was evaluated after 4 weeks of residence time in the greenhouse. Rhizoms and young plants, respectively, of the perennial grasses creeping wheat and Bermuda grass were replanted in pots, allowed to grow for about 4 weeks and subsequently, at a height of about 10 to 15 cm, treated (that is, sprayed) with the compounds of the invention. Evaluation was carried out 4 weeks after the treatment. Also in this test, fluorodifen and mecoprop served as comparative agents. The compounds of the invention had a better effect against annual and perennial grasses according to this application mode than the two comparative agents. The other compounds of the Examples of formulation showed similar herbicidal action.

TABLE II

| Example | (Post-emergence treatment) | | | | |
|---|---|---|---|---|---|
| | kg/ha A.S. | AVF | SAL | LOM | AGR | CDN |
| 1 | 5 | 1 | 1 | 1 | 1 | 1 |
| | 1.2 | 1 | 1 | 1 | — | — |
| 2 | 2.5 | 1 | 1 | 1 | 1 | 5 |
| | 0.6 | 1 | 1 | 3 | — | — |
| 3 | 2.5 | 1 | 1 | 1 | 5 | — |
| | 0.6 | 1 | 1 | 4 | — | — |
| 4 | 2.5 | 11 | 1 | 6 | — | — |
| | 0.6 | 2 | 1 | 7 | — | — |
| 6 | 2.5 | 1 | 1 | 1 | 7 | — |
| | 0.6 | 1 | 1 | 5 | — | — |
| 7 | 2.5 | 1 | 1 | 1 | 1 | 4 |
| | 0.6 | 1 | 1 | 1 | — | — |
| 8 | 2.5 | 1 | 1 | 1 | — | 4 |
| | 0.6 | 1 | 1 | 1 | — | — |
| 9 | 2.5 | 1 | 1 | 1 | — | — |
| | 0.6 | 1 | 1 | 1 | — | — |
| 10 | 2.5 | 1 | 1 | 1 | 1 | 4 |
| | 0.6 | 1 | 1 | 1 | — | — |
| 11 | 2.5 | 1 | 1 | 1 | — | — |
| | 0.6 | 1 | 1 | 1 | — | — |
| 12 | 2.5 | 1 | 1 | 1 | 1 | 4 |
| | 0.6 | 1 | 1 | 1 | — | — |
| 14 | 2.5 | 1 | 1 | 1 | — | — |
| | 0.6 | 1 | 1 | 5 | — | — |
| 15 | 2.5 | 1 | 1 | 1 | — | — |
| | 0.6 | 1 | 1 | 1 | — | — |
| 16 | 2.5 | 1 | 1 | 1 | — | — |
| | 0.6 | 1 | 1 | 1 | — | — |
| 17 | 2.5 | 1 | 1 | 1 | — | 5 |
| | 0.6 | 2 | 1 | 4 | — | — |
| 18 | 2.5 | 1 | 1 | 5 | — | — |
| | 0.6 | 7 | 1 | 8 | — | — |
| 19 | 2.5 | 1 | 1 | 1 | — | — |
| | 0.6 | 1 | 1 | 4 | — | — |
| 20 | 2.5 | 1 | 1 | 1 | 2 | 6 |
| | 0.6 | 1 | 1 | 4 | — | — |
| 21 | 2.5 | 1 | 1 | 1 | — | — |
| | 0.6 | 1 | 1 | 1 | — | — |
| 29 | 2.5 | 1 | 1 | 4 | 4 | 7 |
| | 0.6 | 1 | 1 | 4 | — | — |
| 30 | 2.5 | 1 | 1 | 1 | 5 | 6 |
| | 0.6 | 1 | 1 | 4 | — | — |
| 31 | 2.5 | 1 | 1 | 1 | 5 | 4 |
| | 0.6 | 1 | 1 | 1 | — | — |
| 33 | 2.5 | 1 | 1 | 1 | 1 | 4 |
| | 0.6 | 1 | 1 | 1 | — | — |
| 34 | 2.5 | 1 | 1 | 1 | — | — |
| | 0.6 | 1 | 1 | 1 | — | — |
| 35 | 2.5 | 1 | 1 | 1 | — | 4 |
| | 0.6 | 1 | 1 | 2 | — | — |
| 36 | 2.5 | 1 | 1 | 1 | — | 4 |
| | 0.6 | 1 | 1 | 1 | — | — |
| 38 | 2.5 | 1 | 1 | 1 | — | 4 |
| | 0.6 | 1 | 1 | 1 | — | — |
| Fluorodifen | 2.5 | — | 2 | 6 | 8 | 9 |
| | 0.6 | — | 3 | 8 | 9 | 9 |
| Mecoprop | 2.5 | — | 7 | 8 | 8 | 8 |
| | 0.6 | — | 8 | 9 | 9 | 9 |

(Abbreviations of the weed grasses see Table I)

EXAMPLE III

The preparation cited in Example 21 was tested according to the same methods in the pre- and post-emergence process for various crop plants. The results were evaluated after about 4 weeks (see Table III). The dates prove that the compound of the invention does not damage, or to an insignificant extent only, a great number of crop plants even at a high dosage rate of 2.5 kg/ha. The compound of Example 12, too, has a good selective effect in the cited crop plants.

TABLE III

| Degree of tolerability by crop plants dosages in kg/ha A.S. | | |
|---|---|---|
| | Compound of Example 22 2.5 | |
| Plants | VA | NA |
| Sugar beet | 1 | 3 |
| Sun flower | 1 | 1 |
| Rape | 1 | 2 |
| White cabbage | 1 | 2 |
| Cucumber | 1 | 4 |
| Peanut | 1 | 1 |
| Soybean | 1 | 2 |
| Dwarf bush bean | 1 | 1 |
| Pea | 1 | 1 |
| Horse bean 2 | 1 | 1 |
| Cotton | 1 | 3 |
| Tomato | 1 | 1 |
| Tobacco | 1 | 1 |
| Carrot | 1 | 3 |
| Wheat | 1 | 3 |

VA = pre-emergence
NA = post-emergence

What is claimed is:

1. A compound of the formula $$\text{CF}_3-\text{C}_6\text{H}_3(\text{R})-\text{O}-\text{C}_6\text{H}_4-\text{O}-\text{CH}(\text{CH}_3)-\text{C}(=\text{O})-\text{O}-\text{R}_1$$

I wherein
R is hydrogen or halogen,
R₁ is
(a) linear or branched (C₁–C₁₂)alkyl substituted by phenoxy which may be optionally mono- or trisubstituted by halogen and/or (C₁–C₄)-alkyl, (C₁–C₄)-acyl or a radical of the formulae $$-N\begin{array}{c}R_2\\R_3\end{array} \quad \text{or} \quad \left[-\overset{R_2}{\underset{R_4}{N}}-R_3\right]^{+}Z^{-}$$

II    III (b) cyclohexenyl or phenyl-(C₃–C₄)-alkenyl;
(c) (C₃–C₄)-alkinyl, which may be mono- or disubstituted by linear or branched (C₁–C₄)-alkyl, phenyl or halogenophenyl with the proviso that R₁ cannot be an unsubstituted propargyl or butinyl radical;
(d) a radical of the formulae $$\begin{array}{c}\text{CH}_3\quad\text{CH}_3\\ \text{O}\diagdown\diagup\text{O}\\|\quad\quad\quad|\\-R'_1-\text{CH}-\text{CH}_2\end{array} \quad -R'_1-\text{O}-\text{CO}-R_5$$

IV    V $$-R'_1-\text{O}-\text{CO}-N\begin{array}{c}R_6\\R_2\end{array} \quad \text{or} \quad -R'_1-\text{S(O)}_n-R_6$$

VI    VII or
(e) (C₁–C₂)alkyl substituted by furyl, tetrahydrofuryl, or oxiranyl;
R₂ and R₃ are (C₁–C₄)alkyl,
R₄ is (C₁–C₄)alkyl,
Z is the anion of an inorganic acid,
R₁' is linear or branched (C₁–C₁₂)alkylene,
R₅ is (C₁–C₄)halogenoalkyl or a radical of the formula $$-\underset{\text{CH}_3}{\overset{|}{\text{CH}}}-\text{O}-\text{C}_6\text{H}_4-\text{O}-\text{C}_6\text{H}_4-\text{CF}_3$$

VIII

R₆ is (C₁–C₄)alkyl or phenyl and
n is zero to 2.

2. A compound of the formula $$\text{CF}_3-\text{C}_6\text{H}_3(\text{R})-\text{O}-\text{C}_6\text{H}_4-\text{O}-\text{CH}(\text{CH}_3)-\text{C}(=\text{O})-\text{O}-\text{R}_1$$

I wherein
R is hydrogen or halogen,
R₁ is (C₁–C₂)-alkyl substituted by furyl, tetrahydrofuryl or oxiranyl or (C₁–C₁₂)alkyl substituted by phenoxy which may be substituted by halogen or (C₁–C₄)-alkyl, acyl or a radical of the formula $$\begin{array}{c}\text{CH}_3\quad\text{CH}_3\\ \text{O}\diagdown\diagup\text{O}\\|\quad\quad\quad|\\-R_1'-\text{CH}-\text{CH}_2\end{array}$$

wherein R₁' is (C₁–C₁₂)-alkylene.

3. A compound of the formula:

$$\text{CF}_3-\text{C}_6\text{H}_3(\text{R})-\text{O}-\text{C}_6\text{H}_4-\text{O}-\text{CH}(\text{CH}_3)-\text{C}(=\text{O})-\text{O}-\text{R}_1$$

wherein
R is a hydrogen or halogen,
R₁ is (C₁–C₂)-alkyl substituted by furyl, tetrahydrofuryl, oxiranyl or a radical of the formula:

$$\begin{array}{c}\text{CH}_3\quad\text{CH}_3\\ \text{O}\diagdown\diagup\text{O}\\|\quad\quad\quad|\\-\text{CH}-\text{CH}_2\end{array}$$

4. A 2-[4'-phenoxyphenoxy]-propionic acid derivative of the formula $$\text{CF}_3-\text{C}_6\text{H}_3(\text{R})-\text{O}-\text{C}_6\text{H}_4-\text{O}-\text{CH}(\text{CH}_3)-\text{C}(=\text{O})-\text{O}-\text{R}_1$$

wherein
R is hydrogen or halogen,
R₁ is (C₁–C₂)alkyl substituted by furyl or tetrahydrofuryl.

5. A compound of the formula $$\text{CF}_3-\text{C}_6\text{H}_3(\text{R})-\text{O}-\text{C}_6\text{H}_4-\text{O}-\text{CH}(\text{CH}_3)-\text{C}(=\text{O})-\text{O}-\text{CH}_2-\text{(tetrahydrofuryl)}$$

wherein R is hydrogen or halogen.

6. A compound of the formula

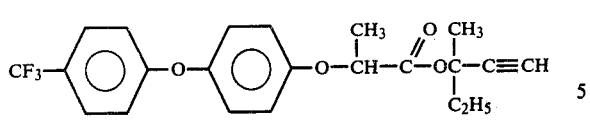

according to claim 1.

7. A compound of the formula

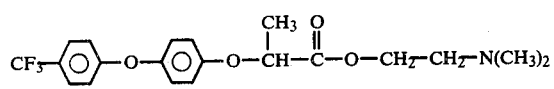

according to claim 1.

8. A compound of the formula

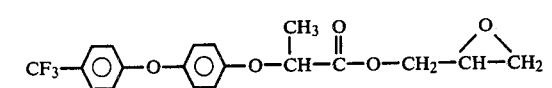

according to claim 1.

9. A compound of the formula

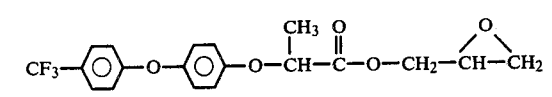

according to claim 2.

10. A compound of the formula

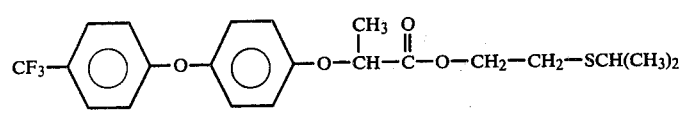

according to claim 3.

11. A compound of the formula

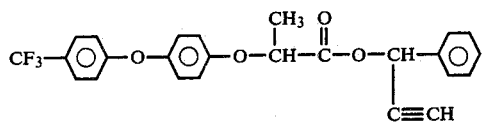

according to claim 1.

12. A compound of the formula

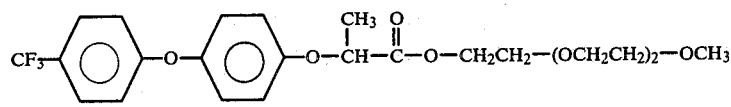

13. A compound of the formula

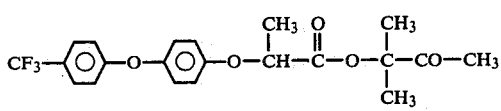

according to claim 2.

14. An herbicidal composition consisting essentially of an inert carrier and an herbicidally effective amount of a compound as defined in claim 1.

15. An herbicidal composition consisting essentially of an inert carrier and an herbicidally effective amount of a compound as defined in claim 2.

16. An herbicidal composition consisting essentially of an inert carrier and an herbicidally effective amount of a compound as defined in claim 3.

17. An herbicidal composition consisting essentially of an inert carrier and an herbicidally effective amount of a compound as defined in claim 4.

18. An herbicidal composition consisting essentially of an inert carrier and an herbicidally effective amount of a compound as defined in claim 5.

19. A method of combating weed grasses which comprises applying to an area containing such weed grasses an herbicidally effective amount of a compound as defined in claim 4.

20. A method of combating weed grasses which comprises applying to an area containing such weed grasses an herbicidally effective amount of a compound as defined in claim 5.

* * * * *